United States Patent
Cummings et al.

(10) Patent No.: US 6,337,323 B2
(45) Date of Patent: Jan. 8, 2002

(54) CHEMICALLY STABLE, INSECTICIDALLY ACTIVE PHOSPHOROMIDOTHIOATE PELLET COMPOSITIONS AND METHODS FOR THEIR MANUFACTURE

(75) Inventors: Gary L. Cummings, Moraga; Young-Jin Lee, Danville; James L. Platt, Jr., San Ramon, all of CA (US); Matthew Hikade; Vernell Stornes, both of Memphis, TN (US)

(73) Assignees: Valent U.S.A. Corporation, Walnut Creek; Tomen Agro, Inc., San Francisco, both of CA (US)

( * ) Notice: Subject to any disclaimer, the term of this patent is extended or adjusted under 35 U.S.C. 154(b) by 0 days.

(21) Appl. No.: 09/259,300

(22) Filed: Mar. 1, 1999

Related U.S. Application Data

(62) Division of application No. 08/992,714, filed on Dec. 17, 1997.
(60) Provisional application No. 60/039,504, filed on Mar. 4, 1997, and provisional application No. 60/033,572, filed on Dec. 19, 1996.

(51) Int. Cl.⁷ .............................................. A01N 57/26
(52) U.S. Cl. ....................... 514/120; 424/405; 424/408
(58) Field of Search ...................... 514/120, 75, 121, 514/124, 129, 131, 134, 135, 137; 424/405, 408

(56) References Cited

U.S. PATENT DOCUMENTS

| | | |
|---|---|---|
| 3,716,600 A | 2/1973 | Magee |
| 3,845,172 A | 10/1974 | Magee |
| 3,914,417 A | 10/1975 | Magee |
| 5,075,058 A | 12/1991 | Chan et al. |
| 5,100,667 A | 3/1992 | Chan et al. |
| 5,298,501 A | 3/1994 | Cummings |
| 5,352,674 A | 10/1994 | Cummings |
| 5,369,100 A | 11/1994 | Cummings |
| 5,443,764 A | 8/1995 | Lloyd et al. |
| 5,464,623 A * | 11/1995 | Chan et al. .................. 424/405 |
| 5,622,658 A | 4/1997 | Lloyd et al. |
| 5,650,163 A | 7/1997 | Cannelongo |

FOREIGN PATENT DOCUMENTS

WO  WO 97/16968  5/1997

OTHER PUBLICATIONS

James A. Polon, Formulation of Pesticidal Dusts, Wettable Powders and Granules, 1973, Pesticide Formulations, 14 pages.

* cited by examiner

*Primary Examiner*—Neil S. Levy

(57) ABSTRACT

Chemically stable, insecticidally active pellets having a low moisture content and at least about 95% active ingredient are described, as well as a method for manufacturing them. The active ingredient is selected from a class of N-hydrocarboyl phosphoroamidothioate and phosphoroamidodithioate compounds as described in the specification. The pellets generally have a moisture content of about 0.5% by weight or less, preferably less than about 0.3% by weight. The pellets can be produced by one of two types of processes as described in detail, including a high pressure axial extrusion process and a low pressure basket extrusion process.

15 Claims, 2 Drawing Sheets

CHEMICALLY STABLE, INSECTICIDALLY ACTIVE PHOSPHOROMIDOTHIOATE PELLET COMPOSITIONS AND METHODS FOR THEIR MANUFACTURE

CROSS-REFERENCE TO RELATED APPLICATIONS

This application claims benefit and priority under 35 U.S.C. § 119(e) of the following two U.S. provisional applications: Ser. No. 60/033,572 filed Dec. 19, 1996, and Ser. No. 60/039,504 filed Mar. 4, 1997, and is a divisional of U.S. application Ser. No. 08/992,714, filed December 17, 1997.

FIELD OF THE INVENTION

The present invention is directed to chemically stable, low moisture content, insecticidally active pellet compositions and methods for their manufacture.

BACKGROUND OF THE INVENTION

Certain phosphoroamidothioates and phosphoroamidodithioates (collectively referred to as "phosphoroamidothioates" for convenience) are known in the art as having excellent insecticidal activity against a variety of insects and in a variety of environments. A particularly important commercial insecticide within this class of compounds is the insecticide acephate (generic name) or Orthene® (trade name), which can be systemically taken up by a plant so that insects which feed and/or live on the plant are killed, in addition to those insects which directly ingest or are contacted by the insecticide. Acephate and related compounds are described in U.S. Pat. Nos. 3,716,600, 3,845,172 and 3,914,417, which disclose that in addition to their insecticidal properties, the compounds possess very low mammalian toxicity. Orthene® is commercially produced as a technical grade chemical of about 97 to 99.5% purity, which is often referred to as acephate technical or acephate TG (technical grade).

Acephate technical is commercially available as a powder, which has a tendency to clump or agglomerate. In the past, acephate technical has been applied to crops as a dust (for example, after exposure to moisture via rain, dew or irrigation), or in spray form as a water solution spray. Dusts are undesirable because of airborne contamination and handling difficulties, while liquid spray formulations involve solvent and packaging expenses, and container disposal requirements that detract from commercial desirability.

Accordingly, in recent years, attention has turned to a pellet form of application for acephate and its related insecticidal compounds. Pellets have the practical advantages of eliminating dust problems and reducing offensive odors in comparison to powder forms because of a reduced surface area to weight ratio.

However, problems have been encountered in these pelletization efforts and to date, high-strength acephate pellets have not been commercialized, most likely due to processing difficulties.

Phosphoroamidothioate-containing pellets have been proposed in U.S. Pat. Nos. 5,075,058, 5,100,667 and 5,464,623, each of which is assigned to Chevron Research and Technology Company. Each of these three patents recognizes the difficulties in pelletizing acephate technical, and proposes certain types of pellets made, for example, by extrusion. For example, the '058 Chevron patent states in the paragraph bridging columns 2–3 that attempts to manufacture acephate technical pellets from acephate technical powder "have heretofore been unsuccessful". Similar statements are made in each of the '667 and '623 Chevron patents. The present inventors have conducted considerable experimentation in the area of producing high-strength acephate pellets, and have confirmed the manufacturing difficulties which the Chevron inventors apparently experienced. Furthermore, the pellets and methods proposed for making them as discussed in the three Chevron patents leave considerable room for improvement. In this regard, while these patents generally describe extrusion of solid pellets, few details of the actual extrusion process are set forth. Moreover, the Chevron patents generally propose the addition of costly surfactants (see '667 patent), the combination of the phosphoroamidothioate with a second active ingredient (see '058 patent), and the creation of a mixture of the active ingredient with a solvent in an amount of from 3–25% by weight before extrusion.

To satisfy the need in the art for a low cost, chemically stable, insecticidally active phosphoroamidothioate granular formulation, one of the present inventors developed an insecticidally active composition comprising particles prepared by the compaction of an admixture comprising ammonium sulfate and at least one insecticidally active phosphoroamidothioate. This composition and methods for its manufacture and use are described in U.S. Pat. Nos. 5,298,501, 5,352,674, and 5,369,100. As set forth in these patents, it was found that the use of ammonium sulfate in particular leads to a compacted composition which provides a high degree of chemical stability.

U.S. Pat. No. 5,443,764 issued Aug. 22, 1995, and related U.S. Pat. No. 5,622,658 issued Apr. 22, 1997, each assigned to ICI Australia Operations Proprietary Ltd., disclose a process for the preparation of water-dispersible granules. The process comprises mixing the desired ingredients of the granules to form an extrudable composition, extruding the mixture and rolling the extrusions to break them down into granules. In contrast to the pellets of the present invention, the granules disclosed in these ICI patents are designed to have rapid dispersion and superior suspensability in water. The granules of the ICI patents comprise an active agricultural chemical (including, e.g., insecticides) and normally have a surfactant component and/or a binding agent. The particular class of insecticidal compounds included in the pellets of the present invention are not disclosed in the ICI patents, although a wide variety of insecticidal active ingredients are stated to be useful.

Thus, there is a need in the art for chemically stable, high strength, insecticidally active phosphoroamidothioate pellets which are useful from a practical standpoint, as well as for a low cost, practical manufacturing technique which can be practiced on a commercial scale without requiring expensive additives or solvents.

SUMMARY OF THE INVENTION

One object of the present invention is to provide chemically stable, high strength, insecticidally active phosphoroamidothioate pellets.

Another object of the present invention is to provide a commercially viable process for manufacturing chemically stable, high strength, insecticidally active phosphoroamidothioate pellets having a low moisture content.

Still another object of the present invention is to provide an economically practical process for producing such insecticidal pellets, which avoids the use of organic solvents and most other additives previously proposed.

The above and other objects and advantages of the present invention can be attained by a process for producing low moisture content pellets comprising an insecticidally active compound of the formula:

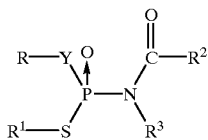

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur, comprising the steps of feeding a powder comprising at least about 95% by weight of said insecticidally active compound to an extruder, feeding water to the extruder during at least a portion of feeding of said powder, the water contacting the powder to form a mixture, extruding an extrusion product while controlling the temperature within the extruder and the rate and quantity of water fed to the extruder to minimize tackiness and clumping together of the extrusion product, and forming pellets having a moisture content of less than about 0.5% by weight from the extrusion product.

As discussed further herein, chemically stable pellets can be manufactured in accordance with the above process. In certain preferred embodiments, the pellets comprise an insecticidal compound as described above, preferably acephate, in an amount of at least about 97% by weight, more preferably virtually 100% by weight, and water in an amount of up to about 0.5% by weight.

In other particularly preferred embodiments, the pellets have a low moisture content sufficient to avoid caking or compaction upon storage. Typically, moisture levels of about 0.3 wt % or less, preferably 0.2 wt % or less, will give unexpectedly good long-term storage properties, assuring flowability of the product.

In addition to the above-described process, chemically stable pellets can be manufactured using a low pressure basket extrusion process, comprising the steps of providing a powder comprising at least about 95% by weight of the above-described insecticidally active compound, contacting the powder with water to form a damp or wet mixture, and thereafter extruding an extrusion product of predetermined diameter from the damp or wet mixture, forming pellets from the extrusion product, and drying the pellets to a moisture content of less than about 0.5% by weight.

Preferably the drying conditions are controlled so that the resultant pellets have a moisture content of less than about 0.3% by weight.

DETAILED DESCRIPTION OF THE INVENTION

Figure 1:
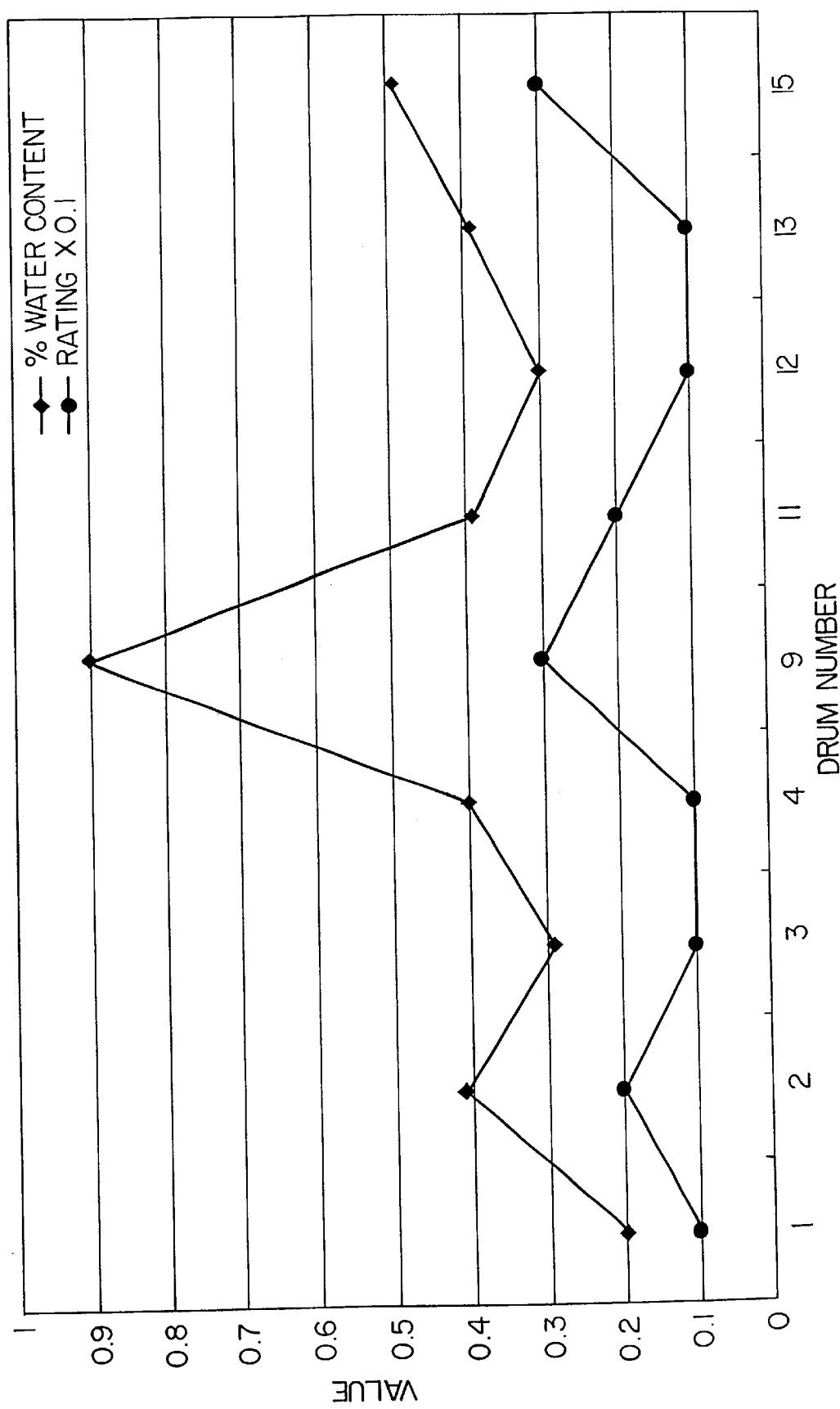
FIG. 1 is graph showing water content vs. flowability for pellet samples stored at 40° C., as discussed in Example 8 below.

In the present invention, the term "phosphoroamidothioate" refers to a compound or a mixture of compounds of the formula:

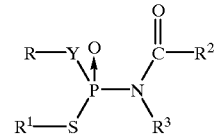

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur. Such compounds are sometimes characterized in the art as N-hydrocarboyl phosphoroamidothioates and phosphoroamidodithioates (see, e.g., U.S. Pat. Nos. 5,075,058, 5,100,667 and 5,464,623 discussed above). It would be apparent to one skilled in the art that the same class of insecticides is intended for use in the present invention as in the patents described in the Background of the Invention.

Particularly preferred compounds for use in the present invention are those in which R and $R^1$ are independently a methyl, ethyl, allyl or alkenyl group; $R^2$ is H or an alkyl group; $R^3$ is hydrogen; and Y is oxygen. The most preferred compound, acephate, is that in which R, $R^1$, and $R^2$ are methyl groups, $R^3$ is hydrogen and Y is oxygen. Compounds of the above formula may be prepared as described in U.S. Pat. Nos. 3,176,600, 3,845,172 and 3,914,417, each of which is incorporated herein by reference in its entirety.

Acephate is commercially available in high strength technical form from Chevron Chemical Company, San Ramon, California. Such high strength acephate technical is sold under the trade name of Orthene® 97SP, typically contains acephate in at least about 97% purity, the remainder being impurities, and is sold as a powder. It is preferred that the active ingredient comprise as close to 100% of the technical powder as possible. Acephate contents of about 99 to 99.5% purity are common and are most preferred. As noted above, acephate technical powder has a tendency to clump and agglomerate over time, and has proven to be difficult to process, as recognized in the art.

One or a mixture of the above compounds forms the insecticidally active component in the pellets of this invention. The present invention is particularly directed to formation of "high strength" phosphoroamidothioate pellets containing a minimum of about 95% by weight active ingredient, preferably at least about 97% by weight active ingredient, and most preferably as close to 100% by weight active ingredient as possible (e.g., in the range of about 99 to 99.5% by weight). The pellets are characterized as having a "low moisture" content, which means that they can contain water in an amount up to about 0.5% by weight. In the present invention, the phrase "up to about 0.5% water" means from relatively small amounts on the order of 0.001% by weight (although moisture measurements at this level are difficult to make, it is believed that even where the pellets are dried to remove moisture or where the pellets are stored under low humidity conditions for a significant time, the pellets do not become completely moisture-free) up to about one-half percent by weight. Moisture amounts generally fall into the range of about 0.05 to about 0.5% by weight, preferably from 0.1 to 0.3% by weight. One of ordinary skill in the art would understand that the upper specified limit is not absolute, however, and that under certain conditions of high humidity and the like, the pellets might absorb moisture in quantities somewhat greater than 0.5%. Nonetheless, in view of moisture's deleterious effects on chemical stability of the pellets, an upper limit in the neighborhood of 0.5% by weight has shown to provide good results. Also, as discussed further below, a pellet moisture content of about 0.3% by weight or less, even more preferably 0.2% by weight or less, is preferred from the standpoint of excellent storage properties.

Further, if desired the pellets can contain small amounts of a processing aid to enhance the ability of the active ingredient to be extruded. For example, extrusion tests have been conducted in which the active ingredient was pre-mixed with about 1.5% by weight of a vinylpyrrolidone-vinyl acetate copolymer (sold under the trade name Agrimer VA-6, available from ISP), and good results were obtained. On the other hand, the pellets of the invention can be suitably manufactured without the need for a surfactant or binding agent, as required in certain prior formulations. Thus, the pellets of this invention are desirable from an economical standpoint. Further, it has been unexpectedly discovered that the phosphoroamidothioate compound can be extruded into chemically stable pellets using only water as a processing aid, under the conditions discussed herein. Accordingly, while small quantities of processing aids other than water, such as Agrimer VA-6 or related vinyl copolymers, can be admixed with the active ingredient prior to extrusion, if desired, in amounts generally ranging from about 0.5% up to several or more percent by weight, the present inventors have determined that chemically stable pellets can be obtained without such processing aids, using acephate technical in particular. One of ordinary skill in the art would readily recognize, however, that minor amounts of processing aids and/or other inert ingredients could be admixed with the active agent, if desired, depending for example on the particular insecticidal compound selected, as long as the addition of such materials did not conflict with or adversely affect the basic characteristics of the pellets formed in accordance with the teachings of the present invention.

In certain preferred forms of the present invention, the pellets consist essentially of acephate technical and water in an amount of up to about 0.5% by weight. Thus, depending on the purity of the technical reagent, it is possible in accordance with the invention to form chemically stable, high strength, insecticidally active phosphoroamidothioate pellets that contain virtually 100% (e.g., 99 to 99.5% or greater) active agent. To the best of the inventors' knowledge, chemically stable pellets of such high strength have heretofore never been manufactured. Such high strength pellets have significant advantages, such as permitting maximum concentrations of insecticidally active agent to be utilized in the field, and excellent stability.

The pellets according to the present invention are typically cylindrically shaped, although they can take on any suitable shape in cross-section (e.g., hexagonal) depending on the shape of the extrusion die orifice. An average diameter of the pellet in cross-section can be from about 1 to about 7 mm, preferably 1.2 to 3 mm. Certain preferred pellets recently extruded using the high-pressure axial extrusion method described herein were cylindrically shaped and had a cross-sectional diameter of about 5/64" (about 2 mm).

The length of the pellets is variable, but typically is in the range of from about 3 mm up to about 25 mm, preferably from about 3 up to about 6 mm.

The pellets produced according to the present invention are chemically stable, and have a commercially satisfactory shelf life on the order of about 2–4 years, during which time they generally remain free-flowing and avoid the raw powder's tendency to agglomerate. As discussed further below, it has now been discovered that excellent flowability can be maintained over time when the pellets are produced so as to have a moisture content of about 0.3 wt % or less. The pellets generally have a white appearance but may have a yellowish tint, and are of sufficient hardness to avoid creation of significant quantities of dust during handling due to pellet crumbling and the like. For pellets produced by the high pressure axial extrusion process described herein, average bulk density has been determined to range from about 36 to about 40 lbs/cubic foot, and typically is about 37 lbs/cubic foot. Using the low pressure type of basket extrusion process also described herein, the average bulk density of the pellets typically ranges from about 28 to about 31 lbs/cubic foot. A significant advantage is that the pellets are preferably formed without the use of organic solvents, as discussed below, and without the use of conventional formulating agents which is not only advantageous economically, but which results in higher strength pellets, while still retaining sufficient physical properties such as hardness and reducing the offensive odors associated with prior powder applications.

Once formulated, the pellets are useful in a method for controlling insects by application of the pellets onto the insects' habitat. In general, the pellets can be applied onto the habitat in an amount sufficient to provide acceptable control of the insects. In a preferred embodiment, the pellets are applied at a rate of at least about 0.5 lbs. active ingredient per acre and more preferably at a rate of from about 0.5 lbs. to about one lbs. active ingredient per acre.

High Pressure Extrusion

The pellets according to the present invention can be manufactured by a high pressure axial extrusion process as follows, using acephate technical as an exemplary insecticidal compound within the scope of the present invention.

Acephate technical powder having a minimum purity of about 97% by weight (preferably 98% or greater, more preferably 99% or greater and most preferably 99.5% or greater purity) is first subjected to a delumping step in a conventional mill or the like, if necessary to reduce or eliminate clumps of material that may have formed due to the material's agglomeration tendency described above. Delumped technical powder provides for better flowability during extrusion.

Next, the delumped acephate technical powder can be blended with a small quantity (e.g., from about 0.5 to about 3.0% by weight) of a processing aid (other than water), such as the Agrimer VA-6 copolymer described above. However, such a step is not necessary to achieve pellets in accordance with the present invention, but may assist flowability during extrusion, particularly for some insecticidal compounds. In some examples described below, a mixture of Orthene® 97SP (lot # R12095, target active ingredient=97.5%, assayed at 99%) and Agrimer VA-6 (lot # CC50907S) was prepared by blending in a mixer at a weight ratio of 2000 lbs/30 lbs=98.5%/1.5%. As described above, however, such processing aids are not essential in practicing the present invention. If desired, however, other processing aids besides Agrimer VA-6 can be used, as would be apparent to one of ordinary skill in the art. The blend thus formed, or the delumped technical, can be stored in drums until needed. Alternatively, delumping and blending, if carried out, can be part of a continuous in-line process.

The acephate technical powder is then placed into a suitable apparatus for supplying the powder to the extruder. The supply can either be continuous over the course of a desired production run, or alternatively, measured batches can be supplied. In one embodiment, the powder feed system to the extruder was an Acrison Auger type feeder, modified with a large feed hopper into which the powder is placed. Using this apparatus the powder feed rate can be controlled as desired by calibrating a variable speed drive before start-up, and controlling the feed rate during operation. During pilot plant tests, the unit was calibrated to allow for a variable flow rate of from about 90 lb/hour to about 250 lb/hour, although it would be understood that actual flow rates during commercial production runs would depend on the particular equipment in use.

In this first embodiment of a process for manufacturing pellets according to the present invention, the extruder is preferably an axial extruder, of which various types are known. In the tests using the modified Acrison Auger type feeder, the extruder was a Bepex 6-inch inch diameter Extrud-o-mixer extructor, a pilot scale model-of which larger versions exist (including one with a 12-inch diameter). The six-inch diameter refers to the diameter of the barrel or screw housing. The extructor includes an outer orifice plate or die located on the front end through which the screw pushes the material through multiple orifices under pressure. If desired, the extructor can also contain an internal orifice plate to improve mixing inside the barrel of the extruder. The holes in the outer orifice plates determine the shape of the extrusion product or extrudate. In most of the tests described herein, the holes were circular of about 2 mm (about 5/64") diameter, which provided extrudate in the form of "noodles" or cylindrical pellets depending on their length.

City tap water can be used as the water source for the process. In the pilot plant runs using the above-described equipment, the water was supplied to the extruder using a tap off of a city-feed line. A flow regulator was installed in the line which allowed regulation and monitoring of the water feed within ranges of from 4 cc/minute (about 0.5 lb/hour) to 50 cc/minute (about 6.6 lb/hour). The point at which the water contacted the powder in the extruder was about six inches downstream from where the powder entered the extruder.

An important aspect of this particular embodiment of the present invention relates to the actual extrusion step. It has been unexpectedly discovered that both the temperature of the extruder barrel during extrusion as well as the rate of water flow are key factors which determine whether commercially viable, high strength acephate pellets can be produced. During extrusion, temperatures inside the barrel tend to increase due to pressure build-up and material mixing. The amount of water added to the powder in the extruder directly affects the temperature inside the barrel. Further, test results have established that the most preferred temperature range within the barrel during extrusion of acephate technical is from about 145° to about 160° F.; within such a range, the acephate material reaches a semi-molten state which has been determined to be important to successful extrusion. At higher temperatures within the extruder, the extruded noodles have a tendency to become too mushy and tacky, and thus stick and clump together. Within the preferred temperature range of about 145–160° F., a preferred rate of water addition was determined to be in the range of about 0.4 up to about 1.0% by weight water, and even more preferably around 0.5% by weight water.

Neither the above-identified preferred temperature ranges or rates of water addition are absolute values. The important concept is one of controlling each of these variables, in tandem, to achieve the desired extrudate which is practically workable. For example, during start-up of the extruder, a higher amount of water should be used until the internal temperature reaches a desired level, at which point the rate of water addition can be decreased to be within the preferred ranges. Further, at higher temperatures it will be seen that lesser quantities of water are needed to give the desired noodle consistency, although at some point the temperature can exceed that at which the extrudate is practically useful because of undue tackiness. Such a point is believed to be reached when the acephate (or other active agent) exceeds its semi-molten state and melts. Of course, the extrusion temperature range preferred for other insecticidal compounds within the scope of the invention will vary depending on the melting point of specific compounds and the quantities of water employed. At lower temperatures within the extruder, the powder is less molten; conversely, a higher rate of water addition is typically required. In some cases, after start-up and with a relatively slow material feed, it may be possible to maintain the temperature within these preferred parameters while reducing water addition to a drip, or stopping it altogether for a portion of a run. In this regard, it will be apparent that the rate at which the powder is fed to the extruder will also impact the internal temperature of the extruder, with a slower rate/lesser quantity developing less internal heat, and a higher rate/greater quantity generating more internal heat.

Thus, a key aspect of the invention is to carry out the extrusion step while controlling the temperature within the extruder and the rate and quantity of water fed to the extruder such that the extrusion product or extrudate has a consistency with minimal stickiness and clumping together. Also, an extrudate which is too wet due to excessive water addition is not preferred because it can lead to stickiness and/or a requirement for excessive drying of the extrudate for a period sufficient to achieve the target moisture level of about 0.5% or less.

To aid in avoiding noodle clumping as the extrudate exits the extrusion die orifice, cooled air can be blown across the outer orifice to accelerate cooling and hardening of the noodles, with resulting decrease in tackiness as they harden. Alternatively, the throughput rate of the material being extruded can be lowered, giving the noodles more time to cool before coming into contact with each other.

The extrusion product formed in the above manner is formed into pellets. This can be done by simply allowing the extrusion product to cool and harden, which will lead to formation of pellets of variable lengths. Alternatively, as the extrusion product exits the die plate, the product can be cut to appropriate size—for example, into more uniformly sized pellets of from 3–10 mm in length.

Drying of the extrusion product can be performed, if desired or as necessary to obtain pellets having a low moisture content. For example, drying is more likely to be carried out on extrusion product formed at or shortly after start-up during which higher quantities of water are generally used and the noodles are wetter.

The dryer can be a vibratory fluid-bed of suitable dimensions with steam-supplied heat. The exhaust is provided by a baghouse that pulls moisture and heat from the extrusion product. Temperature, airflow into, and amount of pull are all variable. The airflow and exhaust are adjusted to provide a fluidized bed of pellets and a slight negative pressure inside the dryer. Temperature is monitored at both the inlet and the outlet of air. The vibrating motion of the drying bed aids in reducing the length of the noodles, which can initially be quite long, but which break down upon cooling and hardening. In some instances a separate mechanical force (e.g., a Stokes delumper) could be applied to assist in breaking down the noodles into shorter pellets as well as breaking up clumps of noodles excessively stuck together, if it is desired to reduce the amount of overs.

The dried pellets can be screened to eliminate fines and overs, if desired. Pellets within the size ranges generally described above can be obtained using an 18-inch Sweco fitted with 6-mesh and 10-mesh screens. Overs and fines can be recycled to the raw material hopper to be fed through the extruder again, if desired.

The following Examples illustrate specific embodiments of the invention but should not be construed as limiting the scope of the claims in any way. In the Examples as well as other parts of this application, all parts, percents, ratios and the like are by weight unless otherwise indicated.

EXAMPLE 1

RUN 9623201

Powder feed was started before the water at a rate of 90 lb/hr. The powder was a 98.5%/1.5% mixture of acephate technical and Agrimer VA-6, as described above. In the past it has proven best to begin extrusion a little on the wet side and slowly decrease the water to the desired rate. The desired rate (1.5%) for the 90 lb/hr of powder was 10 cc/m, or 1.3 lb/hr. The rate used at start-up was between 20 and 30 cc/m (2.6–4.0 lb/hr or 2.8%–4.3%) until noodles were formed. As soon as it was determined the extrusion process (forming noodles) was stable, the water was slowly cut back to between 4 and 10 cc/m. The extrusion process ran steady for over one hour. The material may have been too wet at the start. The initial noodles had a very wet look and had the tendency to stick together. The temperature of the extruder barrel increased considerably as the rate of water was decreased. The extrusion process was running stable.

RUN 9623302

The purpose of this trial was to run continuously for one shift and collect data by monitoring flow rates and temperatures, and taking in-process samples for analytical and chemical analyses. Material was extruded wet at first (2.8%–4.3%) and visually had a very wet look again. Within 15 minutes the rate had been cut back to 5 cc/m (~0.5%) with the powder still feeding at 90 lb/hr. Once again the temperature increased as the moisture decreased. The process ran continuously until it was decided to shut down to add a scraper to the front of the extruder. The purpose of the scraper was to prevent noodles from getting too long and sticking together.

Moisture samples were taken at the extruder and the dryer at 30 minute intervals. The average moisture of the noodles directly out of the extruder was 0.29% with a range of 0.11% to 0.42%. The average moisture of the dryer samples (dryer temp avg: 1300 F) was 0.31% with a range of 0.29% to 0.40%. The table below summarizes the in-process results which include moisture analyses (Mettler weight-loss and Karl Fischer) and assay.

Once the temperature in-the extruder rose to about 150°–160° F., the process could be run while only adding little water. The rate of 5 cc/m was actually only a slow drip of water into the extruder.

The noodles of extruded material did not seem to break from the extruder until they were very long. This raised two concerns: First, though the noodles break up in the dryer and during screening and handling, the longer noodles often do not break up enough to pass through the avers screen during that step. That means a large quantity of overs is actually good pellet product, but just a little longer than the pellets that were screened as product. Second, because of the configuration of the face plate that holds the outer orifice plate in place, the long noodles were getting caught behind the spokes of the face plate and were being bunched up due to the material being pushed out behind. The semi-molten state of the material being extruded contributed to this condition because the material is tacky as it is extruded and noodles already have the tendency to stick together. A fan was positioned so that it blew air across the die plate in order to cool the noodles quicker as they exited the extruder. The fan seemed to reduce the tackiness because the moving air would cause the noodles to cool quicker therefore making them less tacky, thereby preventing them from sticking together. Tackiness could be reduced even more by blowing chilled air across the noodles and/or slowing the feed rate so that the noodles have more time to cool before being pushed forward by material behind.

RUN 9623303

The purpose of this trial was to extrude using a scraper against the outer plate in order to cut the noodles as they were formed therefore preventing them from becoming too long. After Run 9623302 was shut down, the scraper was added quickly without cleaning the holes in the outer plate or clearing the material out of the extruder barrel. The scraper was attached, the face plate was attached and the unit was started up immediately. This all took place in five minutes from the shut down of the previous run. It was not possible to extrude material through the holes of the outer place but material did ooze out from between the shaft of the extruder and the center of the plate where the shaft protrudes. The material hardened as it oozed out creating "potato chip" looking pieces. The unit was shut down for a thorough cleaning.

The material in the extruder and in the holes of the outer plate became very hard when the unit was shut down and had a few minutes to cool. This is consistent with the theory that the material is semi-molten when it is extruded at a low moisture because of the way the material hardened into big blocks as it cooled. It cannot be ruled out however, that the pressure inside the extruder as well as the tendency of Orthene to harden probably also contributed to the hardening effect that was observed.

RUN 9623304

The purpose of this trial was to run with the scraper in place. The extruder was cleared out and the outer plate was cleaned with steam to clear the holes. Extrusion was started on the wet side and noodles were formed but the scraper seemed to "smear" the material across the plate rather than cut the noodles cleanly. This was attributed to the scraper not being strong enough to withstand the pressure of the material being extruded. If a scraper made of a stronger material was used, it might have worked. Too much material was fed to the extruder too quickly and when the pressure became too great inside the barrel the screw seized and the unit was shut down.

RUN 9623305

The purpose of this trial was to prove it was possible to start up again and run for at least an hour. The two previous trials resulted in complications that caused a shut-down of the unit. Start-up went well (similar to Run 9623302) and the process ran for one hour.

Moisture samples were taken at the extruder and dryer. The extruder sample had 0.09% water and the dryer sample had 0.10% water.

RUN 9623306

The purpose of this trial was to test prepare high strength pellets without any processing aids, such as the Agrimer VA-6.

Orthene Technical powder was run immediately following the Orthene/Agrimer mix during Run 9623305. The process ran continuous with no problem; about 50 pounds of Orthene Technical was run. No moisture data is available.

RUN 9623401

The purpose of this trial was to produce pellets with a diameter of 1 mm; up until this point the pellets described in the previous runs had a diameter of 2 mm. All parameters remained the same; feed rate, water feed, dryer temperature, and extruder RPM. Material was extruded wet at first and was slowly dried out (meaning the water feed rate was reduced) until the rate of water addition was at 0.5%. The noodles were visually acceptable until the temperature rose to 180° F. in the extruder. At this point the material was very mushy and the noodles were clumping together. The large "balls" of material were not breaking up in the dryer.

It was attempted to run using no water at all. It is possible but not preferred because of the temperature increase.

In order to decrease the temperature the rate of water feed was increased to 20 cc/m (or 2.6%). The temperature of the extruder dropped to 140° F. but the noodles looked wet and mushy.

The water rate was decreased to 10 cc/m (1.5%) and the temperature rose to 153° F. The noodles did not seem to improve visually.

Before shutting down an experiment was conducted to test the effects of slower feed rate on temperature. The Acrison was turned on and off repeatedly to give the simulation of a slower feed rate (<90 lb/hr). The water feed was kept at less than 4 cc/m and the temperature remained around 140°–150° F. The water feed was terminated and no apparent change in temperature was observed.

Moisture samples at the extruder ranged from 0.40% to 0.62% and the single dryer sample registered a moisture level of 0.19%.

It is seen that the temperature inside the extruder is an important factor. It already has been established that a higher temperature is necessary to set the material in a semi-molten state so that it can be extruded at a low moisture content. From what has been observed with acephate, the temperature in the extruder should preferably be in the range of about 145°–160° F. At higher temperatures the material becomes too mushy and tacky, and have the tendency to stick and clump together.

It seems there are two factors that control temperature in the extruder. The first is the rate of water sprayed on the powder and the second is the rate of powder feed or overall rate of material sent through the extruder. During a production run, the temperature can be influenced using a water jacket on the extruder, if desired.

RUN 9623501

The purpose of this run was to extrude about 300 pounds of Orthene Technical without added processing aids, formulating agents or use of organic solvents. When the 300 pounds was completed the remaining Orthene/Agrimer mix (98.5%:1.5%) would follow without shutting down. The outer plate with the 2-mm diameter holes was used with a dryer temperature of 110° F. After an hour of running, the steam to the dryer coils was cut off and "cool" air (80° F.) was sent through the dryer in order to cool and harden the noodles which were already under 0.5% moisture.

The rater of water feed was settled at 4 cc/m but the powder rate was varied to test the limits of the extruder. The rate was measured by collecting material exiting the extruder for two minutes, weighing, and multiplying the result by 30 to get a rate in pounds per hour. At one point during the run the rate was 240 lbs/hr and by visually judging the look of the noodles at the extruder, this rate was too high. The noodles were being formed too fast and did not have time to cool and harden before coming in contact with each other. Because of this, the noodles were clumping together and were forming chunks that would not break apart in the dryer.

The rate was slowed to 150 lb/hr and noodle quality improved.

The switch from Orthene Technical to Orthene/Agrimer was smooth as expected. There were no changes in the quality of extrusion. The dryer was swept empty during the switch to ensure there was no mixing of material.

Moisture samples were taken periodically from the extruder and the dryer. The average moisture at the extruder was 0.33% and the average moisture of samples at the dryer was 0.30%.

After 2.5 hours of running the unit was shut down.

There are no apparent differences in extrusion of Orthene Technical and the Orthene/Agrimer blend. The pellets of Orthene Technical seem to have a yellowish tint when compared to the bright white look the Orthene/Agrimer pellets possess.

Though a high throughput rate can be run, it is not preferred because of the tendency of the noodles to stick together. A lower rate should be run so that the noodles have time to cool before coming in contact with each other. An alternative would be to blow chilled air across the front of the outer face plate in order to cool and harden the noodles as they are extruded.

RUN 9623502

The purpose of this trial was to finish running the remaining material and to run rework. Rework consisted of screener fines and extruder clean-out. The majority of the rework was added to the Acrison hopper to blend it with the virgin material. A small amount (including some hard material) was added directly into the barrel of the extruder.

The powder was fed at the rate of 90 lb/hr and the water was fed at 4–5 cc/m (0.5%). The system ran for 6 hours before shutting down due to no more material. The process ran smooth with no complications.

Samples were taken every hour with an average extruder moisture of 0.42% (range: 0.19% to 0.99%) and an average dryer moisture of 0.25% (range: 0.20% to 0.31%).

There seemed to be no complications with running rework either by mixing it with virgin material or adding directly to the extruder. The extruder screw did seem to strain a little to push the hard material through the outer plate but there was no visible slow-down in noodle production.

The slower rate did seem to aid in preventing the noodles from clumping together. After the system stabilized at 90 lb/hr and 4 cc/m of water, there did not seem to be much material sticking together at the outer plate of the extruder. This was true for the entire 6 hours.

In all of the above runs, screening was accomplished using a small Sweco fitted with a 6- and a 10-mesh screen. Before the material was screened it was fed through a delumper in order to break up some of the noodles that had stuck together and the long noodles. The delumper did, however, create some fines. The process itself did not create a large amount of fines.

Because a large amount of the overs consisted of good product (longer pellets), the overs were rescreened twice in order to remove the good material.

Pellets from the above runs were packaged in 200 lb fiber drums.

Samples of each drum were collected, and the following physical and chemical analyses were completed: assay; dry sieve, pH, dissolution, friability, bulk density; and moisture. A brief description of the analytical methods is given in Table 1.

TABLE 1

PHYSICAL ANALYSES METHODS

DRY SIEVE

100 Grams
5 minute rotap with hammer
Sieve Stack: 4, 6, 8, 14, 20, 60, Pan (US standard)
Yield: −6/+14

MOISTURE

Mettler Weight-loss balance
2 grams, 60° C., 5 minutes pH

2% Solution
$H_2O$ from tap
Stir 3 minutes

TABLE 1-continued

PHYSICAL ANALYSES METHODS

DISSOLUTION 2 grams in 100 ml graduated cylinder
Record turns - (turn = two 180° inversions)
Record time to dissolve

DENSITY

Fill cylinder, scrape top flat $$\frac{\text{weight in cylinder}}{\text{vol cylinder}} \times 62.43 = \text{lb/ft}^3$$

FRIABILITY

Take −6/+14 cut from dry sieve
100 revolutions on friabilator
Rotap using 20-mesh sieve for 3 minutes with hammer
Weigh fines and product The results are presented in Table 2 below with samples numbers and run numbers being correlated as follows:

| DRUM # | TRIAL RUN |
|---|---|
| A2-126-01 | 9623501 |
| A2-126-02 | 9623306 9623501 |
| A2-126-03 | 9623501 9623502 |
| A2-126-04 | 9623502 9623305 |
| A2-126-05 | 9623302 9623305 |
| A2-126-06 | 9623302 |
| A2-126-07 | 9623201 9623302 |
| A2-126-08 | mixed fines |
| A2-126-09 | mixed oversize |
| A2-126-10 | mixed fines |
| A2-126-11 | 9623401 |

| | SAMPLE | | | | | | | | | | |
|---|---|---|---|---|---|---|---|---|---|---|---|
| | A2-126-01 D# 1 | | A2-126-02 D# 2 | | A2-126-02 D# 2 | | A2-128-03 D# 3 | | A2-126-04 D# 4 | | A2-126-05 D# 5 |
| | Orthene Technical Pellets | | | | | | Orthene 97% Pellets | | | | |
| ASSAY - 97% | 98.2 | | 98.8 | | | | 96.1 | | 98.3 | | 97.0 |
| DRY SIEVE | GRAMS | PER-CENT | GRAMS | PER-CENT | GRAMS | PER-CENT | GRAMS | PER-CENT | GRAMS | PER-CENT | GRAMS | PER-CENT |
| +4 | 0 | 0 | 0 | 0 | | | 0 | 0 | 0 | 0 | 0 | 0 |
| +6 | 1.2 | 1.2 | 0.4 | 0.4 | | | 0.6 | 0.6 | 1.6 | 1.6 | 1.9 | |
| +8 | 58.9 | 58.5 | 43.1 | 43.3 | | | 58.0 | 57.7 | 63.4 | 63.2 | 64.7 | 64. |
| +14 | 39.7 | 39.4 | 55.1 | 55.4 | | | 41.4 | 41.2 | 34.8 | 34.7 | 33.3 | 33.3 |
| +20 | 0.5 | 0.5 | 0.6 | 0.6 | | | 0.1 | 0.1 | 0.2 | 0.2 | 0.1 | 0.1 |
| +60 | 0.1 | 0.1 | 0.1 | 0.1 | | | 0.1 | 0.1 | 0.1 | 0.1 | 0.1 | 0.1 |
| PAN | 0.3 | 0.3 | 0.2 | 0.2 | | | 0.3 | 0.3 | 0.2 | 0.2 | 0.1 | 0.1 |
| Yield - 6/+14 | 100.7 | 97.9 | 99.5 | 98.7 | | | 100.5 | 98.9 | 100.3 | 97.9 | 100.2 | 97.8 |
| pH (2.0%) | 6.09 | | 6.08 | | | | 6.15 | | 6.14 | | 6.12 | |
| | 23 Turns | | 22 turns | | | | 21 Turns | | 18 Turns | | 19 Turns | |
| DISSOLUTION | 138 Sec | | 129 sec | | Rerun | | 119 sec | | 110 sec | | 103 sec | |
| FRIABILITY | 1st | 2nd | 1st | 2nd | | | 1st | 2nd | 1st | 2nd | 1st | 2nd |
| +20 | 98.21 | 98.07 | 98.71 | 98.62 | 98.23 | | 98.07 | 99.17 | 97.50 | 97.98 | 97.59 | 97.59 |
| PAN | 0.05 | 0.01 | 0.03 | 0.01 | 0.01 | | 0.01 | 0.01 | .04 | 0.01 | 0.01 | 0.03 |
| FRI | 0.05 | 0.01 | 0.03 | 0.01 | 0.01 | | 0.01 | 0.01 | .04 | 0.01 | 0.01 | 0.03 |
| DENSITY (#/ft³) | 38.4 | | 38.2 | | | | 39.1 | | 38.9 | | 37.1 | |
| MOISTURE % | 0.48 | | 0.1 | | | | 0.1 | | 0.20 | | 0.10 | |

| | SAMPLE | | | | | | | | | | |
|---|---|---|---|---|---|---|---|---|---|---|---|
| | A2-126-06 D# 6 | | A2-126-07 D# 7 | | A2-126-08 D# 8 | | A2-128-09 D# 9 | | A2-126-10 D# 10 | | A2-126-11 D# 11 |
| | Orthene 97% Pellets | | | | | | Overs | | Fines | | Non-Usable | |
| ASSAY - 97% | 97.2 | | 95.9 | | 98.6 | | 98.1 | | 97.6 | | 97.9 | |
| DRY SIEVE | GRAMS | PER-CENT | GRAMS | PER-CENT | GRAMS | PER-CENT | GRAMS | PER-CENT | GRAMS | PER-CENT | GRAMS | PER-CENT |
| +4 | 0 | 0 | 0 | 0 | 0 | 0 | 1.2 | 1.2 | | | 0 | 0 |
| +6 | 0.6 | 0.6 | 7.6 | 7.6 | 5.7 | 5.7 | 63.3 | 63.3 | | | 1.8 | 1.8 |
| +8 | 53.1 | 53.1 | 64.0 | 63.9 | 76.9 | 76.7 | 33.8 | 33.8 | | | 41.0 | 41.0 |
| +14 | 46.0 | 46.0 | 28.1 | 28.1 | 17.4 | 17.4 | 1.5 | 1.5 | | | 54.4 | 54.3 |
| +20 | 0.1 | 0.1 | 0.2 | 0.2 | 0 | 0 | 0 | 0 | 14.3 | 28.3 | 2.5 | 2.5 |
| +60 | 0.1 | 0.1 | 0.1 | 0.1 | 0.1 | 0.1 | 0.1 | 0.1 | 19.4 | 38.4 | 0.1 | 0.1 |
| PAN | 0.1 | 0.1 | 0.1 | 0.1 | 0.1 | 0.1 | 0.1 | 0.1 | 16.8 | 33.3 | 0.3 | 0.3 |

-continued

| | | | | | | | | | | | |
|---|---|---|---|---|---|---|---|---|---|---|---|
| Yield - 6/+14 | 100 | 99.1 | 100.1 | 92.0 | 100.2 | 94.1 | 100 | 35.3 | 35.3 | 50.5 | 100.1 | 95.3 |
| pH (2.0%) | 6.09 | | 6.13 | | 6.13 | | 6.23 | | 6.14 | | 6.18 | |
| DISSOLUTION | 19 Turns | | 20 Turns | | 20 Turns | | 26 Turns | | | | 20 Turns | |
| | 111 Sec | | 104 sec | | 104 sec | | 143 sec | | | | 97 sec | |
| FRIABILITY | 1st | 2nd | 1st | 2nd | 1st | 2nd | 1st | 2nd | | | 1st | 2nd |
| +20 | 98.58 | 98.26 | 91.58 | 91.48 | 93.89 | 95.06 | 35.23 | 34.62 | | | 45.25 | 94.01 |
| PAN | .04 | .03 | 0.01 | 0.01 | 0.01 | 0.01 | 0.01 | 0.01 | | | 0.01 | 0.03 |
| FRI | .04 | .03 | 0.01 | 0.01 | 0.01 | 0.01 | 0.01 | 0.01 | | | 0.01 | 0.03 |
| DENSITY (#/ft$^3$) | 37.9 | | 37.8 | | 36.8 | | 37.7 | | | | 36.3 | |
| MOISTURE % | 0.10 | | 0.10 | | 0.10 | | 0.20 | | 0.39 | | 0.19 | |

Low Pressure Extrusion

The pellets according to the present invention can also be manufactured using a low pressure basket extrusion process, as described below using acephate technical as an exemplary insecticidal compound within the scope of the present invention.

Low pressure basket extrusion processing has been carried out on a batch scale, as well as on a continuous process scale. For batch processing, the same type of delumped technical powder as described above for the high pressure method can be used. One particular batch of such a "premix" was prepared as follows:

The acephate and the Agrimer VA-6 were mixed in a blender within the above-described proportions, at a 1,000 lb batch size.

Product was blended and delumped through an air classifying hammermill.

Premix was off-loaded into drums.

The low pressure basket extrusion batch process generally involves kneading the premix in a kneader, and adding water in a desired amount. Testing proved that a water content of about 2–7% by weight, preferably about 2.0–3.5% by weight, was optimal to obtain very low moisture content pellets, although higher and lower amounts can be used, as long as the final pellets achieve moisture contents within the specified range. Addition of the water forms a damp or wet mixture.

After kneading, the damp or wet kneaded mixture is placed into the feed hopper of a low pressure basket granulator, such as a commercially available model known as the BR-200 Granulator, and extruded through screens having holes of the desired pellet diameter. The wet, extruded noodles are then carefully dried to the desired moisture content. For this purpose, a fluid bed dryer, such as MDB-400, can be employed. As discussed below, by controlling the drying conditions, pellets having preferred moisture contents of about 0.3% by weight or less, preferably 0.2t by weight or less, can be obtained.

EXAMPLE 2

Specific batches of pellets were prepared using the low pressure basket extrusion, as follows:

5 kg of premix (prepared as in Example 1) was weighed into a KDHJ-20 Batch Kneader. The specified amount of water was poured into the kneader, and the mixture was kneaded (mixed) for 4 minutes.

The kneaded mixture was placed into the feed hopper of a BR-200 Granulator and extruded. The screens had 1 mm diameter holes.

The wet, extruded noodles were swept into a pail for transfer to the dryer.

The extruded noodles were placed into a MDB-400 Fluid Bed Dryer (bed area 0.4306 sq ft).

The drying temperatures were in the range of about 130–140° F. range, and the residence times varied based on moisture content. For the repeat batches (10–25), an 18 min drying time was used.

The raw data from twenty-three batches thus prepared is set forth below:

| Batch | 1 | 2 | 3 | 4 |
|---|---|---|---|---|
| Ingredients | | | | |
| Orthene (g) | 5000 | 5000 | 5000 | 4000 |
| Water (g) | 250 | 250 | 150 | 280 |
| Moisture Level (%) | 4.8 | 4.8 | 2.9 | 6.5 |
| Kneader | KDHJ-20 | KDHJ-20 | KDHJ-20 | KDHJ-20 |
| Time (min) | 4 | 4 | 4 | 4 |
| Power (Kw) | 1.0 | 1.0 | | |
| Bulk Density (kg/l) | | | | |
| Comments | Soft, lumpy mixture | Soft, lumpy mixture | Slightly more powdery than 1 & 2 | Lumpier than 1 & 2 |
| Extruder Type | BR-200 | BR-200 | BR-200 | BR-200 |
| Screen (mm) | 1.0 | 1.0 | 1.0 | 1.0 |
| Thickness (mm) | 1.2 | 1.2 | 1.2 | 1.2 |
| Clearance (mm) | 0.5 | 0.5 | 0.5 | 0.5 |
| Speed (rpm) | 45 | 45 | 45 | 45 |
| Rate (kg/hr) | | 147.3 | 134.5 | 116.3 |
| Power (Kw) | 1.8 | 1.8 | | |
| Granule Temp. (° C.) | Rm. temp. | Rm. temp. | Rm. temp. | Rm. temp. |
| Bulk Density (kg/l) | 0.4432 | 0.4432 | 0.4856 | 0.4976 |
| Comments | Good extrudates | Good extrudates | Good extrudates | Good extrudates |
| Drying | MDB-400 | MDB-400 | MDB-400 | MDB-400 |
| Initial Moisture (%) | 4.8 | 4.8 | 2.9 | 6.5 |
| Drying Time (min) | 7 | 12 | 12 | 25 |
| Final Moisture (%) | 0.8 | 0.5 | 0.2 | 0.1 |
| Final Product Temp. (° C.) | 51 | 54 | | |
| Final Bulk Density (kg/l) | | 0.4768 | 0.747 | 0.5368 |

| Batch | 8 | 9 | 10–14 |
|---|---|---|---|
| Ingredients | | | |
| Orthene (g) | 5000 | 5000 | 5000 |
| Water (g) | 350 | 350 | 350 |
| Moisture Level (%) | 6.5 | 6.5 | 6.5 |
| Kneader | KDHJ-20 | KDHJ-20 | KDHJ-20 |
| Time (min) | 4 | 4 | 4 |
| Power (Kw) | 1.25 | | 1.2 |
| Bulk Density (kg/l) | | | |
| Comments | Soft, lumpy mixture | Same | Same |
| Extruder Type | BR-200 | BR-200 | BR-200 |
| Screen (mm) | 1.0 | 1.0 | 1.0 |
| Thickness (mm) | 1.2 | 1.2 | 1.2 |
| Clearance (mm) | 0.5 | 0.5 | 0.5 |
| Speed (rpm) | 45 | 45 | 45 |
| Rate (kg/hr) | 134.5 | 149.7 | |

-continued

| | | | |
|---|---|---|---|
| Power (Kw) | | | |
| Granule Temp. (° C.) | Rm. temp. | Rm. temp. | |
| Bulk Density (kg/l) | 0.4856 | 0.4590 | |
| Comments | Extrudates left overnight (will) dry next A.M. | Good extrudates *Drying Curve performed on this batch | Good extrudates |
| Drying | MDB-400 | MDB-400* | MDB-400 |
| Initial Moisture (%) | 6.5 | 6.5 | 6.5 |
| Drying Time (min) | 18 | 25 | 18 |
| Final Moisture (%) | 0.11 | 0.10 | |
| Final Product Temp. (° C.) | 45 | 46 | 44 |
| Final Bulk Density (kg/l) | 0.5264 | 0.5176 | |

| Batch | 15–25 | 27 |
|---|---|---|
| Ingredients | | |
| Virgin Orthene (g) | 5000 | 1388 |
| Triton (ml) | 0 | 1388 |
| Water (g) | 350 | 166.5 |
| Moisture Level (%) | 6.5 | 5.7 |
| Kneader | KDHJ-20 | KDHJ-20 |
| Time (min) | 4 | 4 |
| Power (Kw) | 1.2 | 1.0 |
| Bulk Density (kg/l) | | |
| Comments | Same | Lumpy mix |
| Extruder Type | BR-200 | BR-200 |
| Screen (mm) | 1.0 | 1.0 |
| Thickness (mm) | 1.2 | 1.2 |
| Clearance (mm) | 0.5 | 0.5 |
| Speed (rpm) | 45 | 45 |
| Rate (kg/hr) | | |
| Power (Kw) | | |
| Granule Temp. (° C.) | | |
| Bulk Density (kg/l) | | |
| Comments | Good extrudates | Good extrudates |
| Drying | MDB-400 | MDB-400 |
| Initial Moisture (%) | 6.5 | 5.7 |
| Drying Time (min) | 18 | 11 |
| Final Moisture (%) | | |
| Final Product Temp. (° C.) | 44 | 45 |
| Final Bulk Density (kg/l) | | |

Product quality data were developed with sample data from-three batches: 2, 12 & 15. The test procedures are the same as outlined in Example 1 above.

| Sample | Batch 2 | Batch 12 | Batch 15 |
|---|---|---|---|
| Assay, acephate | 97.1 | 97.7 | 98.2 |
| Moisture, % | 0.1 | 0.1 | 0.1 |

-continued

| Sample | Batch 2 | Batch 12 | Batch 15 |
|---|---|---|---|
| Dissolution, turns | 4 | 3 | 3 |
| Dry Sieve, % | | | |
| +8 | 0.4 | 0.1 | 0.3 |
| +60 | 99.4 | 99.8 | 99.6 |
| −60 | 0.2 | 0.1 | 0.1 |
| Friability, % | 0.23 | 0.01 | 0.004 |

EXAMPLE 3

Continuous processing using the low pressure basket extrusion process can be carried out as follows. The same premix technique to prepare a delumped powder as described above in Example 1 was employed. A typical batch size was about 2030 lbs. The continuous process is summarized below:

Drums of premix are discharged into an elevator, and premix is transferred into a blender.

Premix is lifted to another blender. This blender feeds an Acrison powder meter/feeder (140-P).

Premix is fed through the Acrison (140-P) into a kneader (LCI 5BM-57). Water (about 3.5–5%) is monitored onto the powder bed in the kneader. The damp feed falls from the kneader into the extruder (LCI BR-200 Granulator).

A pump and flow meter are used to control the water addition to the premix. The water and powder flow rates are controlled independently by the operators. Samples of the kneaded mixtures are assayed for water content on a ¼ or ½ hour schedule. Water contents were varied (3–5.5.%), with the operators targeting a water content of about 4–5%.

The damp premix is extruded through 1.2 or 1.5 mm screens. The extruded "noodles" are swept off of the extruder into a dryer.

The movement of the noodles from the screen exit to the entry of the dryer and then through the dryer, which breaks the noodles into pellets of varying length.

The pellets are dried in an 8 sq. ft. fluid bed dryer. Air inlet temperatures are maintained at about 130–140° F., with a target of 135F.

Dried product is discharged into a screener (Sweco LS60C8888), set with 6 and 20 mesh screens. Oversize material (+6 mesh) is discarded. Undersize material (−40 mesh) is recycled into premix.

Table 3 below provides data from thirty-one lots produced as described above:

TABLE 3

| Lot No. | % Acephate | Dry Sieve | | | | | | % Disp | % Water content | % FRIA. | pH | Bulk Dens | Pellet |
|---|---|---|---|---|---|---|---|---|---|---|---|---|---|
| | | +6 | +8 | +20 | +40 | 60 | −60 | | | | | | |
| 1 | 99.2 | 0 | 0.1 | 95.2 | 4.5 | 0.1 | 0.1 | 5 | 0.30 | 0.34 | 5.91 | 29.4 | 1.2 MM |
| 2 | 97.2 | 0 | 0.2 | 99.0 | 0.6 | 0.0 | 0.2 | 6 | 0.50 | 0.35 | 5.99 | 28.4 | 1.5 MM |
| 3 | 99.0 | 0 | 0.2 | 96.6 | 3.0 | 0.1 | 0.1 | 6 | 0.45 | 0.33 | 6.00 | 30.5 | 1.2 MM |
| 4 | 98.4 | 0 | 0.1 | 96.4 | 2.9 | 0.4 | 0.2 | 5 | 0.10 | 0.33 | 5.98 | 30.4 | 1.2 MM |
| 5 | 98.7 | 0 | 0.1 | 97.0 | 2.4 | 0.3 | 0.2 | 5 | 0.30 | 0.33 | 5.99 | 29.1 | 1.2 MM |
| 6 | 97.1 | 0 | 0.1 | 98.2 | 1.2 | 0.1 | 0.4 | 8 | 0.49 | 0.33 | 6.02 | 28.7 | 1.5 MM |
| 7 | 96.0 | 0 | 0.2 | 96.8 | 2.3 | 0.2 | 0.5 | 5 | 0.30 | 0.33 | 6.02 | 28.5 | 1.5 MM |

TABLE 3-continued

| Lot No. | % Acephate | Dry Sieve +6 | +8 | +20 | +40 | 60 | −60 | % Water Disp | % content | FRIA. | pH | Bulk Dens | Pellet |
|---|---|---|---|---|---|---|---|---|---|---|---|---|---|
| 8  | 97.2 | 0 | 0.2 | 98.9 | 0.7  | 0.1 | 0.1 | 6 | 0.30 | 0.33 | 5.68 | 30.8 | 1.5 MM |
| 9  | 97.8 | 0 | 0.1 | 99.3 | 0.5  | 0.0 | 0.1 | 7 | 0.30 | 0.33 | 6.00 | 30.1 | 1.5 MM |
| 10 | 96.5 | 0 | 0.3 | 97.9 | 1.4  | 0.2 | 0.2 | 5 | 0.40 | 0.66 | 6.05 | 29.6 | 1.5 MM |
| 11 | 98.6 | 0 | 0.2 | 97.4 | 1.8  | 0.4 | 0.2 | 7 | 0.50 | 0.33 | 5.98 | 30.1 | 1.5 MM |
| 12 | 96.3 | 0 | 0.2 | 99.4 | 0.3  | 0.0 | 0.1 | 5 | 0.40 | 0.33 | 6.02 | 30.6 | 1.5 MM |
| 13 | 97.5 | 0 | 0.1 | 97.4 | 2.3  | 0.1 | 0.1 | 5 | 0.50 | 0.33 | 6.08 | 28.7 | 1.2 MM |
| 14 | 97.3 | 0 | 0.1 | 91.6 | 7.8  | 0.3 | 0.2 | 6 | 0.20 | 0.33 | 6.07 | 28.2 | 1.2 MM |
| 15 | 97.0 | 0 | 0.1 | 91.7 | 7.5  | 0.3 | 0.4 | 5 | 0.30 | 0.33 | 6.06 | 29.5 |  |
| 16 | 98.5 | 0 | 0.1 | 89.8 | 9.2  | 0.7 | 0.2 | 6 | 0.30 | 0.33 | 6.07 | 30.1 | 1.2 MM |
| 17 | 98.0 | 0 | 0.1 | 87.0 | 12.4 | 0.3 | 0.2 | 4 | 0.29 | 0.33 | 5.97 | 28.7 | 1.2 MM |
| 18 | 97.1 | 0 | 0.1 | 88.2 | 11.4 | 0.1 | 0.2 | 6 | 0.47 | 0.33 | 6.05 | 28.8 | 1.2 MM |
| 19 | 97.1 | 0 | 0.1 | 96.2 | 3.5  | 0.1 | 0.1 | 6 | 0.19 | 0.33 | 5.97 | 26.3 | 1.2 MM |
| 20 | 96.7 | 0 | 0.1 | 98.2 | 1.4  | 0.1 | 0.2 | 6 | 0.20 | 0.33 | 5.98 | 29.7 | 1.2 MM |
| 21 | 96.0 | 0 | 0.1 | 96.6 | 2.8  | 0.3 | 0.2 | 6 | 0.10 | 0.66 | 5.99 | 29.5 | 1.2 MM |
| 22 | 97.1 | 0 | 0.1 | 97.7 | 1.9  | 0.1 | 0.2 | 6 | 0.19 | 0.33 | 6.01 | 28.6 | 1.2 MM |
| 23 | 99.2 | 0 | 0.1 | 97.8 | 1.9  | 0.1 | 0.1 | 7 | 0.39 | 0.33 | 5.81 | 30.7 | 1.2 MM |
| 24 | 98.1 | 0 | 0.1 | 99.1 | 0.7  | 0.0 | 0.1 | 4 | 0.50 | 0.33 | 6.07 | 29.8 | 1.2 MM |
| 25 | 97.0 | 0 | 0.1 | 97.6 | 2.0  | 0.1 | 0.2 | 5 | 0.30 | 0.66 | 5.99 | 27.8 | 1.5 MM |
| 26 | 98.3 | 0 | 0.1 | 97.6 | 1.9  | 0.2 | 0.2 | 7 | 0.39 | 0.33 | 6.00 | 29.6 | 1.5 MM |
| 27 | 98.4 | 0 | 0.1 | 94.8 | 3.1  | 1.8 | 0.2 | 6 | 0.20 | 0.66 | 6.01 | 28.7 | 1.2 MM |
| 28 | 97.0 | 0 | 0.2 | 95.9 | 3.2  | 0.5 | 0.2 | 5 | 0.50 | 0.33 | 5.81 | 30.4 | 1.2 MM |
| 29 | 97.5 | 0 | 0.1 | 98.4 | 1.3  | 0.1 | 0.1 | 7 | 0.29 | 0.34 | 6.08 | 28.5 | 1.2 MM |
| 30 | 97.1 | 0 | 0.0 | 97.7 | 1.7  | 0.4 | 0.2 | 9 | 0.28 | 0.34 | 5.96 | 28.6 | 1.2 MM |
| 31 | 98.5 | 0 | 0.2 | 97.5 | 1.8  | 0.3 | 0.2 | 5 | 0.50 | 0.33 | 5.81 |  |  |

In the above samples, the average acephate content was 97.59 weight %, well within the target content of 96% minimum acephate. The other characteristics shown above were generally within target ranges.

Using the above-described continuous processing based on principles of low pressure basket extrusion, particularly preferred pellets can be obtained which have the following physical properties and/or characteristics (see Table 1 above for description of physical analyses methods):

| | |
|---|---|
| appearance | white to cream color pellets |
| sieve analysis | 0.1% maximum +8 mesh |
| | 0.2% maximum −60 mesh |
| | 99.8% within +8/−60 mesh |
| acephate | at least about 96 wt %, preferably at least 97 wt % |
| moisture | less than about .3 wt %, preferably less than .2 wt % |
| dissolution | 12 inversions, maximum |
| friability | 0.5% maximum, −40 mesh |
| bulk density | about 26–31 lbs./cu.ft. |
| pellet size | about 1.2–1.5 mm. |

The bulk densities for the preferred pellets produced by the low pressure extrusion process generally are lower than for the samples produced using the high pressure axial extrusion process described above. The preferred pellets are typically about 3 to 6 mm in length. The diameter is determined by the pore diameter in the screens of the basket extruder used in the manufacturing process. Particle length is determined by breakage of the extrudate as it exits the extruder and travels through a fluid bed dryer. A set of sieves at the final stage of the process excludes fines and large particles. Typically pellet preparations are sufficiently uniform that over 95% are captured on a 20 mesh screen which retains the 3–6 mm range pellet.

As would be understand by one of ordinary skill in the art, the pellets of the present invention can contain other, optional ingredients, such as dyes, pigments and reodorants. The following example demonstrates this feature.

EXAMPLE 4

Pellets were produced by the following laboratory procedure.

Acephate technical and Agrimer VA-6 were dry blended in a jar in the amounts shown in Table 4 below.

The mixture was twice passed through a small hammermill to delump the acephate and for further blending.

The resulting powder mixture was transferred to a Cuisenart Pro Custom 11 food processor. Water (6 wt %) was added, and the mixture was stirred until a uniform damp mixture was obtained.

The damp mix was added to an LCI Benchtop Granulator, fitted with screens with 1.5 mm diameter holes.

The mixture was extruded, and the extruded mix was dried in an Aromatic Fluid Bed Laboratory Unit STREA I. The drying conditions were about 140° F., full air flow and 45 minute residence time.

In the preparation of the pellets, dyes, pigments and reodorants were added to either the processing water (W) or to the powder premix (P), as shown in Table 4 (amounts in wt %). Both blue and black dyes (Pylam Products Victoria Blue B, Acid Blue 9, Acid Black 2), a pigment (Pylam Products Pigment Blue 29), and reodorant systems (Stepan Toximul 3406F and Quest N-6574) were tested as to their effects on the pellets.

TABLE 4

| | Sample | | | | | | |
|---|---|---|---|---|---|---|---|
| | A | B | C | D | E | F | G |
| Acephate technical | 98.35 | 98.35 | 98.35 | 98.35 | 98.35 | 98.00 | 98.30 |
| Agrimer VA-6 | 1.50 | 1.50 | 1.50 | 1.50 | 1.50 | 1.50 | 1.50 |
| Pigment Blue 29 | 0.015 | — | — | — | — | — | — |
| Victoria Blue B | — | 0.015 | 0.015 | — | — | — | — |
| Acid Blue 9 | — | — | — | 0.015 | — | — | — |
| Acid Black 2 | — | — | — | — | 0.015 | — | — |
| Toximul 3406F | — | — | — | — | — | 0.925 | 0.010 |
| N-6574 | — | — | — | — | — | 0.025 | 0.010 |
| Additive Assay | P | W | P | W | W | W | W |

Table 5 below shows measured properties of Samples A–G to which the dyes, pigment or reodorant had been added. In each instance, the physical properties including hardness, appearance, etc. were acceptable.

TABLE 5

| | Sample | | | | | | |
|---|---|---|---|---|---|---|---|
| | A | B | C | D | E | F | G |
| Assay, acephate (%) | 97.5 | 98.0 | 97.5 | 98.3 | 96.9 | 98.1 | 98.1 |
| Dissolution, number | 9 | 10 | 9 | 10 | 11 | 10 | 10 |
| Moisture | 0.29 | 0.26 | 0.27 | 0.30 | 0.27 | 0.13 | 0.19 |

Although the above samples show that various optional ingredients are compatible with the Orthene pellets in amounts of about 0.025–0.015 wt %, greater or lesser amounts can be used, as desired. Generally, however, such additives are present in total amounts of less than about 1 wt %, preferably about 0.5 wt % or less, more preferably 0.25 wt % or less, and even more preferably 0.1 wt % or less. For example, a batch of pellets was prepared using 0.015 wt % Victoria Blue B, which worked well to dye the pellets to the desired color, without adversely influencing the physical properties or characteristics.

EXAMPLE 6

Shelf life data from certain of the samples obtained according to Example 3 above, and whose physical characteristics are set forth in Table 3 above, are provided in Table 6 below:

TABLE 6

| Lot # | 1 | 2 | 4 | 9 | 11 | 24 |
|---|---|---|---|---|---|---|
| Moisture % | 0.30 | 0.50 | 0.10 | 0.30 | 0.50 | 0.50 |
| Storage Temperature, Assay, % acephate | | | | | | |
| Plant Assay 1 Month | 99.2 | 97.2 | 98.4 | 97.8 | 98.6 | 98.1 |
| Refrigerator | 98.0 | 97.6 | 98.9 | 98.4 | 98.1 | 98.6 |
| 40° C. | 97.6 | 96.0 | 98.2 | 98.1 | 98.0 | 97.9 |
| 50° C. | 97.5 | 96.7 | 97.5 | 97.7 | 96.5 | 97.4 |

TABLE 6-continued

| Lot # | 1 | 2 | 4 | 9 | 11 | 24 |
|---|---|---|---|---|---|---|
| 2 Month | | | | | | |
| 30° C. | 97.4 | 97.1 | 97.2 | 97.6 | 98.1 | 97.7 |
| 40° C. | 97.2 | 96.8 | 97.7 | 98.9 | 96.3 | 97.5 |
| 3 Month | | | | | | |
| Ambient lab | 97.3 | 98.5 | 97.2 | 98.4 | 98.1 | 98.6 |
| 30° C. | 97.4 | 98.3 | 97.4 | 97.8 | 98.2 | 97.0 |
| 40° C. | 98.2 | 95.7 | 97.5 | 97.3 | 96.0 | 96.0 |
| 10 Month Ambient lab | 97.6 | 98.0 | 97.6 | 98.0 | 97.7 | 97.6 |
| Storage Temperature, Dissolution, Number of Inversions | | | | | | |
| 10 Month Ambient lab | 11 | 10 | 10 | 11 | 9 | 10 |
| Storage Temperature, Physical appearance | | | | | | |
| 10 Month Ambient lab | All samples have retained the white, pellet shaped appearance | | | | | |

The data in Table 6 demonstrate acceptable shelf life, both chemically and physically.

EXAMPLE 7

Additional testing has been performed using a low pressure, continuous basket extrusion process. It has now been determined that the pellets of the present invention exhibit more preferred characteristics relating to storage stability and anti-caking and flowability properties at moisture levels below about 0.3 wt %, preferably below 0.2 wt %. These low moisture content pellets can be attained by appropriate adjustment of the process parameters, including the drying conditions.

Orthene pellets were made by the following procedure, similar to that described above in Example 3.

The same premix (acephate technical and Agrimer VA-6) preparation procedure was employed. See Example 1.

Drums of premix were charged into a blender.

The blender feeds a feed screw for powder addition to the kneader, an LCI 5BM-57.

Water was metered to the kneader. Pressurized bottles (not a pump as in Example 3) provided the constant rate of water flow. A spray nozzle distributed the water onto the powder bed within the kneader. The damp acephate/ Agrimer feed fell by gravity into the basket extruder, an LCI BR-450 Granulator.

The water content was controlled so as to give a preferred moisture content of about 2.0 to 3.5 wt % of the kneaded mixture. In this example, the preferred water content is lower than that specified above for Example 3 (in Example 3, water content varied from 3–5.5 wt %, with a target water content of about 4–4.5 wt %)

The extrusion and drier operational description was the same as set forth in Example 3, except that the product was dried in a 21 sq. ft., three-zone fluid bed dryer. Typically, the first two zones had a drying temperature of about 130–140° F., with the third zone operating at lower temperatures, generally from about 115–125° F. Overall drying time varies, but the pellets can typically pass through the three zones in about 10–15 minutes.

The dried pellets were discharged from the dryer into a bucket elevator for transfer into a holding bin. Thereafter, the pellets were fed to the screener described in Example 3, and processed as described therein. It is preferred to ensure that the pellets have cooled to below about 95° F. prior to screening and packaging.

To achieve the preferred target moisture content of about 0.29 wt % or less, control of the water content in the kneading step as well as the drying step is important. With some samples, a second pass through the dryer was necessary. One of ordinary skill in the art would be able to determine the appropriate specific conditions to obtain the target moisture level given the guidance provided herein. The results from 17 lots produced using this procedure are set forth in Table 7 below:

flowing. This compaction, referred to as caking or lumping, is not preferred from a commercial standpoint, because aliquots must be poured from the drums for repackaging or for preparing spray solutions.

Compaction is considered to be the product of certain variables. Moisture content has been determined to be the most important variable affecting compaction relative to the typical product storage conditions of 20–40° C. Elevated temperatures, e.g., 50° C., exacerbate the caking problem.

By evaluation of various pellet lots which had been stored at temperatures of up to about 35° C. for over six months, we determined that at moisture contents of about 0.3 wt % and above, the pellets were generally caked to the extent that the pellets would not flow freely from the drum. Thus, it is preferred that the moisture content of the pellets be controlled to amounts less than about 0.3 wt %, more preferably less than about 0.2 wt %, to eliminate or substantially reduce compaction over time under typical storage conditions.

14 and 28 day accelerated aging tests were conducted to assess the role of water, temperature, and package size on the caking phenomenon. Package size was evaluated to assess the role of pressure on caking. For example, pellets in the lower portion of an 80 kg drum experience greater pressure than in a 40 kg or 20 kg drum. The aging test consisted of 18 drums of pellets manufactured using the low pressure basket extrusion process generally described above. Nine drums were stored at 40° C. and nine at 50° C. Drums were selected from two typical production lots and assigned the category "Lot A" or "Lot B". The moisture content of the pellets in each drum was assayed at the start of the test, and the contents of each drum were passed through a screen of 0.25 inch opening to assure that the pellets were cake-free at the start of the test. A range of container sizes were evalu-

TABLE 7

| Lot # | % Acephate | % Moisture | pH | Disp | Bulk Den | Dry +6 | +8 | Sieve +8/−60 | −60 | % FRIA. |
|---|---|---|---|---|---|---|---|---|---|---|
| 3237-P01 | 98.8 | 0.29 | 5.8 | 7 | 30.3 | 0 | 0.1 | 99.7 | 0.2 | 0.13 |
| 3237-P02 | 97.8 | 0.28 | 5.85 | 7 | 30. | 0 | 0.1 | 99.7 | 0.2 | 0.1 |
| 3237-P03 | 98 | 0.13 | 5.9 | 8 | 30.8 | 0 | 0.1 | 99.7 | 0.2 | 0.13 |
| 3297-P04 | 99 | 0.19 | 5.88 | 7 | 30.3 | 0 | 0.1 | 99.8 | 0.1 | 0.13 |
| 3297-P05 | 97.4 | 0.13 | 5.75 | 8 | 30.8 | 0 | 0.1 | 99.8 | 0.1 | 0.17 |
| 3337-P06 | 97.5 | 0.2 | 5.84 | 8 | 28.8 | 0 | 0.2 | 99.5 | 0.2 | 0.33 |
| 3337-P07 | 98.6 | 0.29 | 5.82 | 5 | 28.3 | 0 | 0.1 | 99.7 | 0.2 | 0.1 |
| 3347-P08 | 97.6 | 0.19 | 5.85 | 5 | 29.2 | 0 | 0.1 | 99.7 | 0.2 | 0.23 |
| 3347-P09 | 97.3 | 0.23 | 5.79 | 5 | 28.1 | 0 | 0.1 | 99.7 | 0.2 | 0.23 |
| 3347-P10 | 97.7 | 0.14 | 5.82 | 4 | 28.7 | 0 | 0.1 | 99.7 | 0.2 | 0.3 |
| 3347-P11 | 96.5 | 0.19 | 5.77 | 8 | 28.3 | 0 | 0.1 | 99.7 | 0.2 | 0.27 |
| 3347-P12 | 96.8 | 0.16 | 5.64 | 5 | 28.8 | 0 | 0.1 | 99.4 | 0.2 | 0.63 |
| 3347-P13 | 98.5 | 0.19 | 5.76 | 4 | 26.9 | 0 | 0.1 | 99.7 | 0.2 | 0.84 |
| 3347-P14 | 98.7 | 0.14 | 3.87 | 5 | 27.8 | 0 | 0.1 | 99.7 | 0.2 | 0.8 |
| 3377-P15 | 98 | 0.22 | 3.98 | 5 | 28.4 | 0 | 0.1 | 99.7 | 0.2 | 0.47 |
| 3377-P16 | 98.7 | 0.15 | 4.03 | 5 | 27.8 | 0 | 0.1 | 99.8 | 0.2 | 0.4 |
| 3377-P17 | 96.7 | 0.24 | 4.22 | 4 | 27.8 | 0 | 0.1 | 99.6 | 0.3 | 0.4 |

EXAMPLE 8

This example demonstrates the ability of low-moisture content acephate pellets to alleviate caking, lumping and compaction problems.

As noted above, the acephate pellets of the present invention are high concentration, free-flowing, dust-free formulations which are water-soluble. Certain of the lots produced in Example 3 were packaged in 80 kg drums. An inspection approximately two months later showed that certain drums had compacted to approximately two-thirds their original volume and the product was no longer free ated: full drum, 80 kg; half full drum, 40 kg; and a quarter drum, 20 kg. Moisture content was measured at the end of each test period. A summary of the test protocol is as follows:

| Two Week Test | |
|---|---|
| 40° C. | 50° C. |
| Drum 1, Lot A 80 kg | Drum 5, Lot A 80 kg |

-continued

| | |
|---|---|
| Drum 2, Lot B 80 kg | Drum 6, Lot B 80 kg |
| Drum 3, Lot A 40 kg | Drum 7, Lot A 40 kg |
| Drum 4, Lot B 40 kg | Drum 8, Lot B 40 kg |
| Four Week Test | |
| 40° C. | 50° C. |
| Drum 9, Lot A 80 kg | Drum 14, Lot A 80 kg |
| Drum 10, Lot B 80 kg | Drum 15, Lot B 80 kg |
| Drum 11, Lot A 40 kg | Drum 16, Lot A 40 kg |
| Drum 12, Lot B 40 kg | Drum 17, Lot B 40 kg |
| Drum 13, Lot A 20 kg | Drum 18, Lot B 20 kg |

A rating scale was developed to evaluate the verity of caking and identify which drums would be acceptable for shipping to customers, as follows:

1=Free flowing, acceptable for shipping

2=Fragile cakes/lumps, sufficiently fragile they break apart upon pouring, acceptable for shipping 3=Caking that prevents pouring, unacceptable for shipping The results are shown in Table 8 below, and in FIGS. 1 and 2.

TABLE 8

| Sample # | End of Test Water [%] | Rating | Lot | Drum # Protocol | Storage Time Weeks | Temp. (C) | Weight (kg) |
|---|---|---|---|---|---|---|---|
| 17-T | 0.2 | 1 | Control | | | | |
| 17-M | 0.3 | 1 | Control | | | | |
| 17-B | 0.3 | 1 | Control | | | | |
| 15 | 0.2 | 1 | A | 1 | 2 | 40 | 80 |
| 18 | 0.41 | 2 | B | 2 | 2 | 40 | 80 |
| 19 | 0.29 | 1 | A | 3 | 2 | 40 | 40 |
| 20 | 0.4 | 1 | B | 4 | 2 | 40 | 40 |
| 4 | 0.39 | 2.5 | A | 5 | 2 | 50 | 80 |
| 6 | 0.4 | 3 | B | 6 | 2 | 50 | 80 |
| 3 | 0.3 | 1 | A | 7 | 2 | 50 | 40 |
| 5 | 0.4 | 2.5 | B | 8 | 2 | 50 | 40 |
| 12 | 0.9 | 3 | A | 9 | 4 | 40 | 80 |
| 8 | 0.6 | 3 | B | 10 | 4 | 50 | 80 |
| 1 | 0.39 | 2 | A | 11 | 4 | 40 | 40 |
| 13 | 0.3 | 1 | B | 12 | 4 | 40 | 40 |
| 14 | 0.39 | 1 | A | 13 | 4 | 40 | 20 |
| 9 | 0.6 | 3 | A | 14 | 4 | 50 | 80 |
| 2 | 0.49 | 3 | B | 15 | 4 | 40 | 80 |
| 7 | 0.4 | 1.5 | A | 16 | 4 | 50 | 40 |
| 11 | 0.3 | 2 | B | 17 | 4 | 50 | 40 |
| 10 | 0.4 | 2 | B | 18 | 4 | 50 | 20 |
| 17 | 0.3 | — | A | 1-B | 2 | 40 | 80 |
| 16 | 0.3 | — | A | 1-M | 2 | 40 | 80 |
| V-1 | 0.2 | 1.5 | — | 1 | 12 | 40 | 80 |
| V-2 | 0.59 | 2 | — | 2 | 12 | 40 | 80 |
| V-3 | 0.3 | 3 | — | 3 | 12 | 50 | 80 |
| V-4 | 0.39 | 3 | — | 4 | 12 | 50 | 80 |

Figure 2:
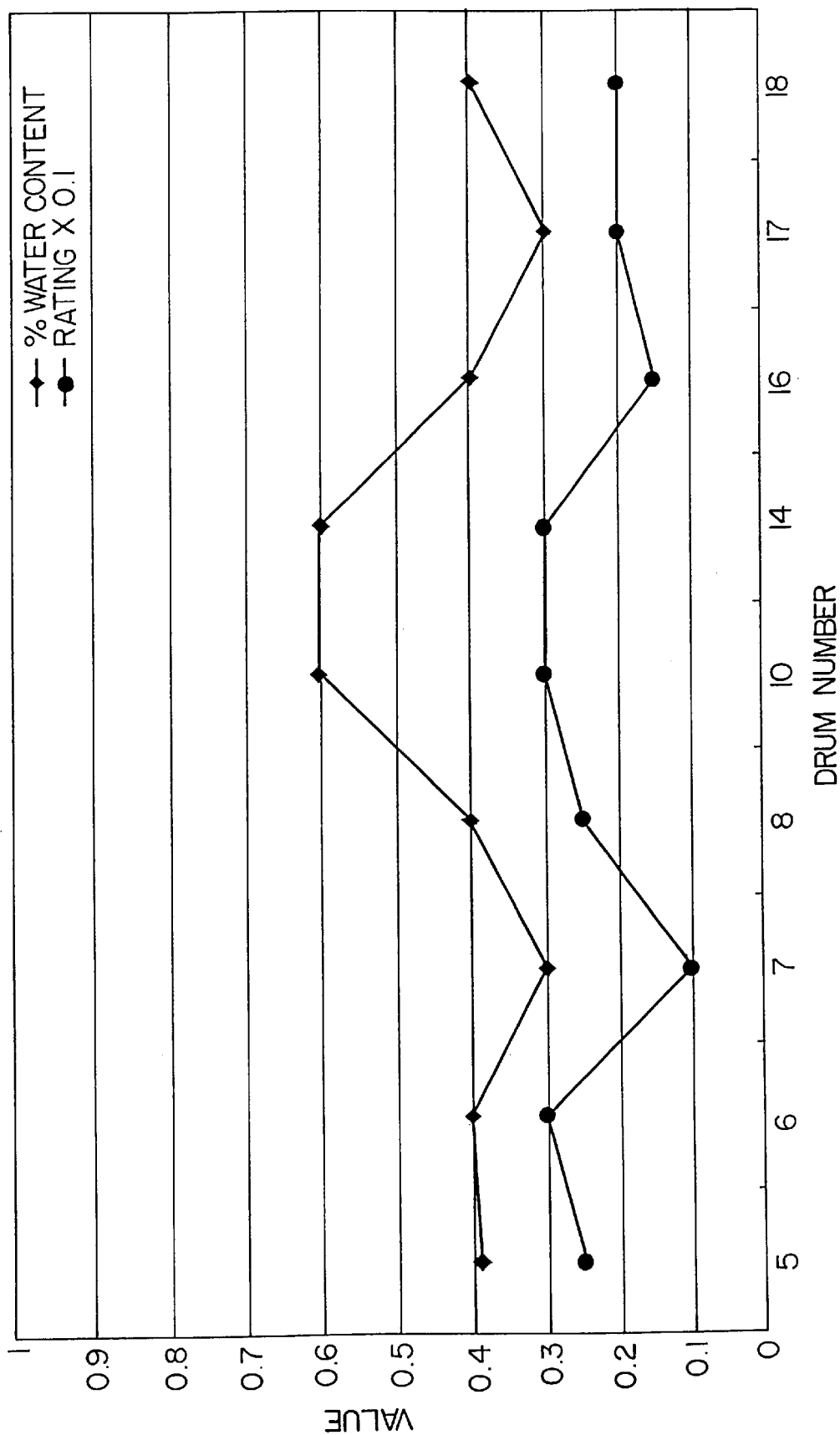
FIG. 2 is graph showing water content vs. flowability for pellet samples stored at 50° C., as discussed in Example 8 below.

FIG. 1 shows the results at 40° C. and FIG. 2 at 50° C. In each graph the upper curve is the water content in weight percent and the lower curve is rating, multiplied by 0.1 to give a value that is conveniently plotted on the same scale as water percentage, i.e., a 0.1 is free flowing, 0.2 fragile lumps and 0.3 unacceptable lumping. Clearly there is a strong correlation between water content and caking for each temperature. A positive correlation between package weight and caking is less clear and a correlation between storage time and caking is not evident.

Samples V-1 to V-4 show the results of a 90 day packaging test that included four 80 kg drums. The results were consistent with the other results shown in Table 8 e.g., at 40° C. a 0.59% water Orthene Pellet had more caking than a 0.20% water sample, the latter being the more acceptable material. At 50° C. for 90 days both a 0.30 and 0.39% water pellet showed caking to an extent that rendered the samples unacceptable. This is not unexpected for a 90 day 50° C. test.

Importantly the caking phenomenon does not lead to product decomposition or physical breakdown of the pellet. Manually breaking the cakes by pressing them through a ¼-inch screen followed by drying to less than 0.3% water gives a free flowing product with virtually no generation of fines or dust.

In summary we find that <0.30% water for storage at less than 40° C. and particularly less than 30° C. assures that the pellets according to the present invention will remain free flowing.

While the invention has been described in detail and with reference to specific embodiments thereof, it will be apparent to one skilled in the art that various changes and modifications can be made therein without departing from the spirit and scope thereof.

What is claimed is:

1. Chemically stable insecticidal pellets consisting essentially of acephate as an active compound, up to about 3% by weight of a vinylpyrrolidone-vinyl acetate copolymer as a processing aid, and water in an amount up to about 0.3% by weight, said pellets having a bulk density of about 26–31 lbs/ft$^3$.

2. The chemically stable insectical pellets according to claim 1, wherein said acephate is present in an amount of about 97 to 99.5% by weight.

3. Chemically stable, low moisture content pellets having a bulk density of about 26–31 lbs/ft$^3$, comprising an insecticidally active compound and up to about 0.3% by weight water, said compound being of the formula:

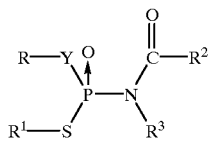

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur, said pellets having been made by a process comprising the steps of
providing a powder comprising at least about 95% by weight of the insecticidally active compound,
contacting the powder with water to form a damp or wet mixture, and thereafter extruding an extrusion product from the damp or wet mixture,
forming pellets from the extrusion product, and
drying the pellets to a moisture content of less than about 0.3% by weight, wherein the process is carried out in the absence of organic solvents.

4. The chemically stable, low moisture content pellets according to claim 3, wherein the powder is contacted with water in an amount of from about 2 to 7% by weight.

5. The chemically stable, low moisture content pellets according to claim 4, wherein the powder is contacted with water in an amount of from about 2.0 to 3.5% by weight.

6. The chemically stable, low moisture content pellets according to claim 3, wherein the pellets are dried to a final moisture content of less than about 0.2% by weight.

7. The chemically stable, low moisture content pellets according to claim 3, wherein the extruding step is carried out using a low pressure basket extruder.

8. The chemically stable, low moisture content pellets according to claim 3, wherein the powder comprises from about 0.5% to about 3.0% by weight of a processing aid other than water.

9. The chemically stable, low moisture content pellets according to claim 8, wherein the processing aid is a vinylpyrrolidone-vinyl acetate copolymer.

10. The chemically stable, low moisture content pellets according to claim 8, further comprising blending the insecticidal compound and the processing aid to form the powder.

11. The chemically stable, low moisture content pellets according to claim 3, wherein R and $R^1$ are independently methyl, ethyl, alkyl or alkenyl; $R^2$ is hydrogen or alkyl; $R^3$ is hydrogen, and Y is oxygen.

12. The chemically stable, low moisture content pellets according to claim 3, wherein R, $R^1$ and $R^2$ are methyl.

13. The chemically stable, low moisture content pellets according to claim 1, wherein the powder consists essentially of acephate technical grade containing at least about 97% acephate, and the resulting pellets are cylindrically shaped and consist essentially of acephate and less about 0.3% by weight water.

14. The chemically stable, low moisture content pellets according to claim 3, wherein said powder consists essentially of acephate technical grade containing at least about 97% acephate.

15. The chemically stable, low moisture content pellets according to claim 3, wherein the process is carried out in the absence of surfactants.

* * * * *